United States Patent
Kyung

(10) Patent No.: US 6,575,740 B2
(45) Date of Patent: Jun. 10, 2003

(54) ORTHODONTIC BRACKET POSITIONING SYSTEM FOR LINGUAL ORTHODONTIC TREATMENT

(76) Inventor: Hee M. Kyung, Ulzi Apt. 101-803, 314-2 Beomeo 4 Dong, Susung, Taegu (KR)

( * ) Notice: Subject to any disclaimer, the term of this patent is extended or adjusted under 35 U.S.C. 154(b) by 25 days.

(21) Appl. No.: 10/034,240

(22) Filed: Dec. 27, 2001

(65) Prior Publication Data

US 2002/0086263 A1 Jul. 4, 2002

(30) Foreign Application Priority Data

Dec. 29, 2000 (KR) .................................. 2000-0036946

(51) Int. Cl.[7] .................................................. A61C 3/00
(52) U.S. Cl. ............................................. 433/3; 433/24
(58) Field of Search .............................. 433/2, 3, 24, 9

(56) References Cited

U.S. PATENT DOCUMENTS

| | | | | |
|---|---|---|---|---|
| 1,082,052 A | * | 12/1913 | Strang | |
| 3,439,421 A | * | 4/1969 | Perkowski | |
| 3,949,478 A | * | 4/1976 | Schinhammer | |
| 4,183,141 A | * | 1/1980 | Dellinger et al. | |
| 4,431,409 A | * | 2/1984 | Picard | 433/2 |
| 5,055,038 A | * | 10/1991 | Ronay et al. | 433/24 |
| 5,059,118 A | * | 10/1991 | Breads et al. | 433/6 |
| 5,064,368 A | * | 11/1991 | Lavin | 433/2 |
| 5,100,316 A | * | 3/1992 | Wildman | 433/24 |
| 5,295,886 A | * | 3/1994 | Wildman | 433/24 |
| 5,791,896 A | * | 8/1998 | Ipenburg | 433/3 |
| 6,123,544 A | * | 9/2000 | Cleary | 433/24 |
| 6,296,481 B1 | * | 10/2001 | Kyung | 433/3 |

* cited by examiner

*Primary Examiner*—Ralph A. Lewis
(74) *Attorney, Agent, or Firm*—Park & Sutton LLP; John K. Park

(57) ABSTRACT

An orthodontic bracket positioning system comprises a plate having a bridge. The plate is defined by a first side portion and a second side portion to form a hollow therebetween. The first and second side portions are connected to each other by the bridge and an outer edge line of the plate contains therein the bridge, the first and second side portions. First and second connectors each have a front end and a rear end to become rotatably engaged to each other between the front and rear ends thereof. The first and second connector front ends are rotatably connected to the first and second side portions An actuator is engaged to said each rear end of the first and second connectors to control a relative rotation of the first and second connectors so as to subsequently either widen or narrow the hollow.

16 Claims, 5 Drawing Sheets

ORTHODONTIC BRACKET POSITIONING SYSTEM FOR LINGUAL ORTHODONTIC TREATMENT

CLAIMING FOREIGN PRIORITY

The applicant claims and requests a foreign priority, through the Paris Convention for the Protection of Industry Property, based on a patent application filed in the Republic of Korea (South Korea) with the filing date of Dec. 29, 2000, with the application number 20-2000-0036946, by the applicant. (See the Attached Declaration)

BACKGROUND OF THE INVENTION

The present invention relates to an orthodontic treatment system. More particularly, the invention relates to an orthodontic bracket positioning system for a lingual (invisible) orthodontic treatment that enables a simultaneous bracket positioning in a simple format.

An orthodontic treatment to improve the alignment of the teeth in the patients mouth generally includes a direct bracket bonding method and an indirect bracket bonding method. For the direct bonding, a plurality of brackets are bonded on target teeth sides within an orthodontic patient's oral cavity. For the conventional indirect bonding, the orthodontic brackets are initially attached to a plaster model with eye-watching to realize a more precise bracket position and then transferred into the oral cavity to bond the brackets onto target teeth sides. However, it is not easy to get an accurate bracket position even on the plaster model especially in lingual sides without using any kind of instrument.

In an effort to improve accuracy of the lingual bracket positioning, Korea Patent Application No. 1998-008587 and subsequent Korea Utility Model Application No. 1999-30664 have been disclosed by the present inventor where an elongated slot is formed along an edge portion of a horizontal metal plate. FIG. 5 shows a brief mechanism of a conventional bracket positioner according to the above Korea Utility Model. As shown therein, the conventional bracket positioner includes a metallic plate 50 having side slots 51 and a front hole 51'. Side bracket holders 54 having connection openings 52 are engaged to the slots 51. A front bracket holder 54 is engaged to the hole 51' with an opening 52' thereof. Brackets 57 are engaged to slots 55, 56 of each bracket holder 53, 54.

However, the brackets 57 cannot be simultaneously bonded on target teeth so separate adjustments have been disadvantageously required for positions and angles. Further, possibility of torque errors has still remained high. Especially, it has been difficult to form an arc outline along target teeth when applied to a straight wire technique.

SUMMARY OF THE INVENTION

The present invention is contrived to overcome the conventional disadvantages and others. Accordingly, it is an object of the present invention to provide an orthodontic bracket positioning system that enables a simultaneous bracket positioning by use of a simplified single form of bracket positioning plate. Another object is to allow the plate to become adjustable sidewise so that patients with wide or narrow arcs of teeth alignment can be treated by simply narrowing or widening a hollow formed through the plate.

To achieve the above-described objects, the orthodontic bracket positioning system according to the present invention comprises a plate having a bridge. The plate is defined by a first side portion and a second side portion to form a hollow therebetween. The first and second side portions are connected to each other by the bridge. An outer edge line of the plate contains therein the bridge, the first and second side portions. The system also includes first and second connectors each having a front end and a rear end. The first and second connectors are rotatably engaged to each other between the front and rear ends thereof. The first connector front end is rotatably connected to the first side portion and the second connector front end is rotatably connected to the second side portion of the plate.

In an embodiment, an actuator is engaged to said each rear end of the first and second connectors to control a relative rotation of the first and second connectors so as to subsequently either widen or narrow the hollow, whereby a bracket attachment from the outer edge line to inner sides of target teeth for an orthodontic treatment is accomplished in an easy, simple and simultaneous format. For a better performance, the orthodontic bracket positioning system comprises a frame having a control arm to facilitate the bracket attachment. The control arm is detachably engaged to the actuator for accuracy and stabilization of the bracket attachment.

The actuator includes a support having a mid portion, a first end and a second end. The first and second ends are sequentially engaged to the respective rear ends of the first and second connectors so a rotation of the support enables the rear ends of the first and second connectors to become either closer to or farther from each other. The support is threaded on and along the first and second ends thereof such that helical threadings of the threaded first and second ends are opposed to each other in direction.

Advantages of the orthodontic bracket positioning system are numerous in that: (1) the plate serving as a bracket positioner enables a simultaneous bracket alignment on inner sides of a patient's teeth by forming the same in a whole structure while substantially decreasing requirement of angle or position adjustments; (2) the hollow formed throughout the plate allows each side portion of the plate to relatively become either narrower or wider by an easy manipulation of the actuator, thereby enabling the plate to easily become adjustable to different people each having a different size of oral cavity; and (3) a conventional difficulty in process of arc-wiring along the inner sides of the patient's teeth during application of a straight wire technique is easily overcome by bracket positioning stabilization realized by the simplified, simultaneous bracket positioning format, further decreasing occurrences of uneven torque on the patient's teeth.

Although the present invention is briefly summarized, the fuller understanding of the invention can be obtained by the following drawings, detailed description and appended claims.

BRIEF DESCRIPTION OF DRAWINGS

These and other features, aspects and advantages of the present invention will become better understood with reference to the accompanying drawings, wherein.

DETAILED DESCRIPTION OF THE PREFERRED EMBODIMENTS

Figure 1:
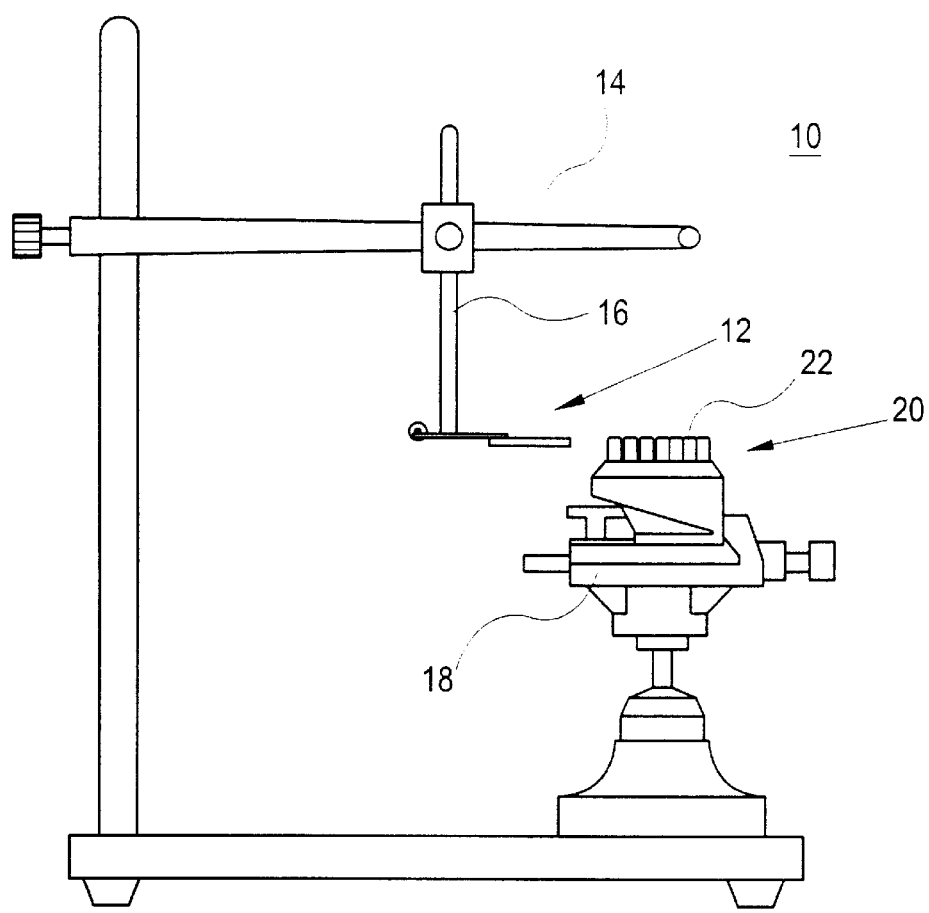
FIG. 1 is a front view showing a mechanism of an orthodontic bracket positioning system according to an embodiment of the present invention.

As shown in FIG. 1, an orthodontic bracket positioning system 10 according to the present invention includes a bracket positioner 12 and a frame 14. The frame 14 includes a control arm 16 and a base seat 18. A plaster model 20 is placed on the base seat 18 to work with the bracket positioner 12. The control arm 16 serves to control the mounting of the bracket positioner 12 on the plaster model 20 which is molded out from an orthodontic patient's oral cavity (not shown). Here, the control arm 16 is adjustable to move vertically and horizontally when required.

Specifically, when an orthodontic patient elects to take a lingual orthodontic treatment, such a plaster model 20 is initially molded out from the patient and placed on the base seat 18 of the frame 14. The lingual orthodontic treatment is also known as an invisible treatment since the orthodontic treatment is almost completely blocked by the patient's teeth and therefore the treatment is not seen from outside. That is, inner sides of the patient's teeth instead of their visible outer sides are used for the orthodontic bracket alignment and wiring. Once the plaster model 20 is obtained from the target patient and placed on the base seat 18 of the frame 14, then the bracket positioner 12 is operated by the control arm 16 to align with target teeth 22 of the plaster teeth model 20 for a bracket attachment.

Figure 2:
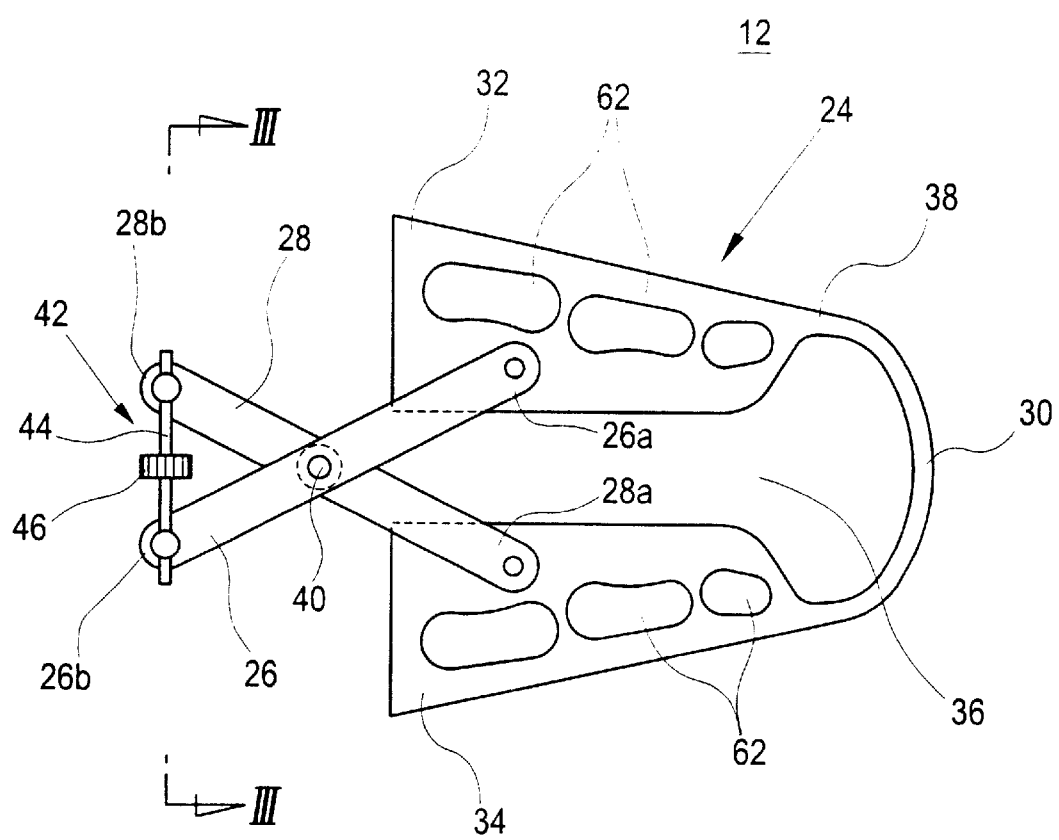
FIG. 2 is a plan view of an orthodontic bracket positioning system according to another embodiment of the present invention.

FIG. 2 shows a construction of the bracket positioner 12. As shown therein, the bracket positioner 12 comprises a plate 24, first and second connectors 26, 28. The plate 24 includes a bridge 30. The plate 24 is defined by a first side portion 32 and a second side portion 34 to form a hollow 36 therebetween. The first and second side portions 32, 34 are connected to each other by the bridge 30. In this construction, an outer edge line 38 of the plate 24 contains therein the bridge 30, the first and second side portions 32, 34.

The first and second connectors 26, 28 each have a front end 26a, 28a and a rear end 26b, 28b. The first and second connectors 26, 28 are rotatably engaged to each other between the front ends 26a, 28a and the rear ends 26b, 28b thereof. An engagement pin 40 is provided to rotatably attach the connectors 26, 28 so as to facilitate the relative rotation of the connectors 26, 28. Meanwhile, the first connector front end 26a is rotatably connected to the first side portion 32 and the second connector front end 28a is rotatably connected to the second side portion 34 of the plate 24.

The orthodontic bracket positioning system 10 further comprises an actuator 42 to control either widening or narrowing the plate 24 via the connectors 26, 28. That is, the first side portion 32 and the second side portion 34 connected to each other by the bridge 30 may become either closer to or farther from each other depending upon the control of the actuator 42. This flexible mechanism of the plate 24 is urged by manipulation of the actuator 42 so that the plate 24 may fit in an oral cavity of whoever requires a lingual orthodontic treatment.

Figure 3:
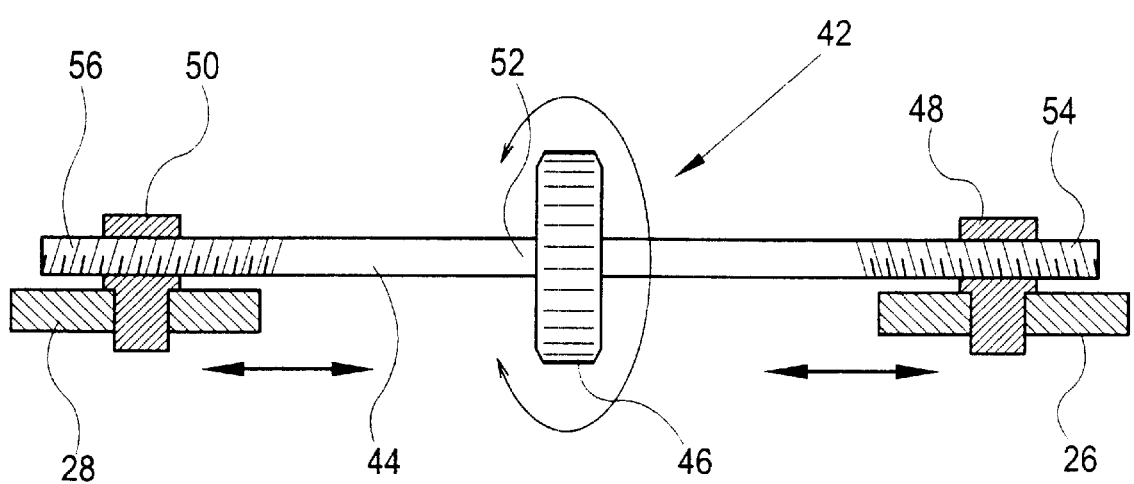
FIG. 3 is a partially cross-sectional view taken along line III—III in FIG. 2.

As further shown in FIG. 3, the actuator 42 comprises a support 44, a handle 46 and a pair of joints 48, 50. The support 44 preferably in shape of a cylindrical rod has a mid portion 52, a first end 54 and a second end 56. The first and second ends 54, 56 are sequentially engaged to the respective rear ends 26b, 28b in a threading mechanism via the joints 48, 50. So a rotation of the support 44 enables the rear ends 26b, 28b of the first and second connectors 26, 28 to become either closer to or farther from each other. Specifically, the support 44 is threaded on and along the first and second ends 54, 56 thereof so helical threadings of the threaded first and second ends 54, 56 through the joints 48, 50 are opposed to each other in direction. Also, the handle 46 fixed between the first and second ends 54, 56 to the support serves to easily manipulate the rotation of the support 44. In a better version, the handle 46 is carried on the mid portion 52 of the support 44.

In order to either narrow or widen the hollow 36 between the first and second side portions 32, 34 of the plate 24, the handle 46 may be rotated such that the connectors 26, 28 rotate relative to the engagement pin 40 that cross-engages the connectors 26, 28, thereby either narrowing or widening the hollow 36 in the plate 24. For example, the handle 46 is rolled up to widen the hollow 36 or rolled down to narrow the hollow 36 between the first and second side portions 32, 34 of the plate 24. The handle 46 may be detachably engaged to the control arm 16 of the frame 14 as shown back in FIG. 1.

Figure 4:
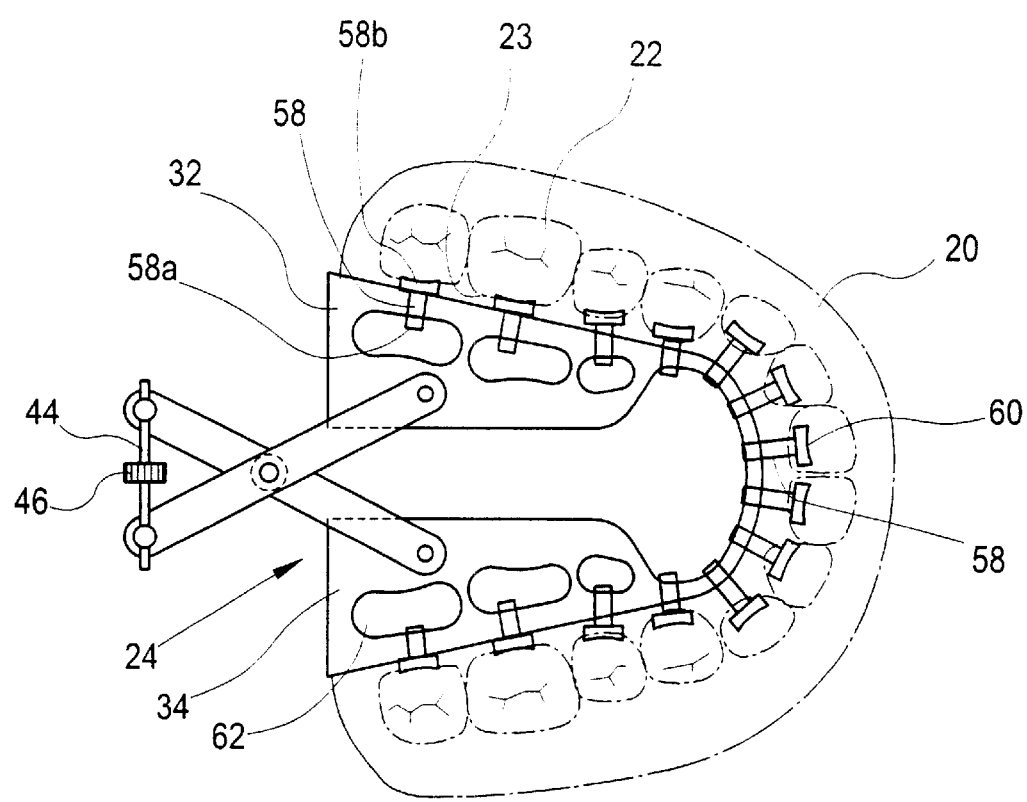
FIG. 4 is a plan view showing an bracket positioning according to the present invention.
Figure 5:
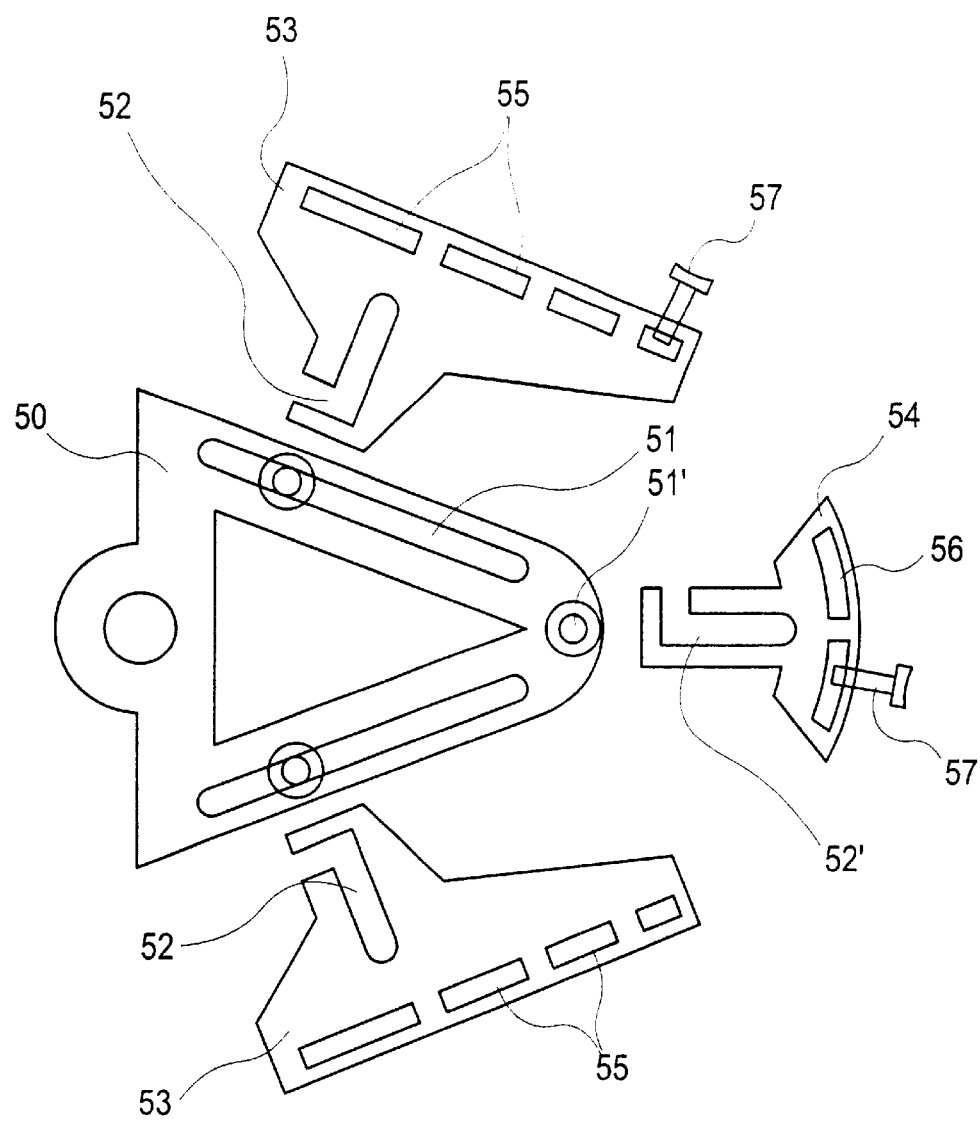
FIG. 5 is an exploded view showing a conventional bracket positioner.

FIG. 4 shows the bracket positioner 12 mounted inside the target teeth 22 in the plaster model 20 that is molded out from inside a mouth of an orthodontic patient. As shown therein, brackets 58 are aligned between the outer edge line 38 of the plate 24 and each inner side 23 of the target teeth 22. Here, brackets 58 vary depending on orthodontic requirements. Each bracket 58 has a known groove 58a on one side thereof to receive a wire (not shown) and a known face 58b on the other side to glue thereby on a selected inner side 23 of the target teeth 22.

In order to mount the plate 24 with the brackets 58 for the bracket positioning on the inner sides 23 of the target teeth 22, the outer edge line 38 of the plate 24 is detachable inserted in each groove 58a of the brackets 58. Using the control arm 16 of the frame 14 that enhances accuracy and stabilization of the bracket attachment, the bracket positioner 12 is mounted such that the brackets 58 along the bridge 30 may reach the inner sides 23 of front teeth of the target teeth 22. Then, the hollow 36 between the first and second side portions 32, 34 of the plate 24 is narrowed or widened by the control of the handle 46 of the actuator 42. That is, if the patient has a wider-than-normal oral cavity, the handle 46 is rolled up to further distance the rear ends 26b, 28b of the connectors 26, 28 to thereby widen the hollow 36 until the corresponding brackets 58 carried on the outer edge line 38 of the plate 24 reach the corresponding inner sides 23 of the target teeth 22. Also, by rolling down the handle 46, the plate 24 with the brackets 58 may be adjusted to fit for a narrower oral cavity of an orthodontic patient.

Once the bracket faces 58b are aligned along the inner sides 23 of the target teeth 22 of the plaster model 20 in a state in which the bracket grooves 58a are worn on and along the outer edge line 38 of the plate 24, each bracket face 58b is attached using a resin 60 to a corresponding inner side 23 of the target teeth 22. Then wait until the resin 60 becomes hardened and detach the plate 24 from the bracket grooves 58a. Thereafter, the brackets 58 are detached from the target teeth 22 using a transfer tray (not shown). Eventually, the bracket faces 58b with the resin 60 thereon become engraved in shape of each curvature of the inner sides of the real teeth (not shown) of the orthodontic patient who wants a lingual or invisible orthodontic treatment. Each resin-hardened bracket 58 in accordance with the teeth inner side curvature of the orthodontic patient is then easily, accurately bonded on each required portion of the inner sides of the patient's teeth.

For a better performance, each side portion 32, 34 of the plate 24 includes one or more openings 62 therethrough to facilitate the bracket insertion and positioning along the outer ridge line 38 of the plate 24. Preferably, the plate 24 is formed of a metallic material in a construction in which the bridge 30 is shaped in an arc and substantially equivalent to each side portion 32, 34 of the plate 24 in thickness.

An advantage of the orthodontic bracket positioning system is that the plate 24 to perform a bracket positioning enables a simultaneous bracket alignment on inner sides of a patient's teeth by forming the same in a whole structure while substantially decreasing requirement of angle or position adjustments. Further, the hollow formed throughout the plate allows each side portion of the plate to relatively become either narrower or wider by an easy manipulation of the actuator, thereby enabling the plate to easily become adjustable to different people each having a different size of oral cavity. In addition, a conventional difficulty in process of arc-wiring along the inner sides of the patient's teeth during application of a straight wire technique is easily overcome by bracket positioning stabilization realized by the simplified, simultaneous bracket positioning format, further decreasing occurrences of uneven torque on the patient's teeth.

Although the invention has been described in considerable detail with reference to certain preferred versions thereof, other versions are possible by converting the aforementioned construction. Therefore, the scope of the invention shall not be limited by the specification detailed above and the appended claims.

What is claimed is:

1. An orthodontic bracket positioning system comprising:
a) a plate having a bridge, wherein the plate is defined by a first side portion and a second side portion to form a hollow therebetween, wherein the first and second side portions are connected to each other by the bridge, wherein an outer edge line of the plate contains therein the bridge, the first and second side portions;
b) first and second connectors each having a front end and a rear end, wherein the first and second connectors are rotatably engaged to each other between the front and rear ends thereof, wherein the first connector front end is rotatably connected to the first side portion and the second connector front end is rotatably connected to the second side portion of the plate; and
c) an actuator engaged to said each rear end of the first and second connectors to control a relative rotation of the first and second connectors so as to subsequently either widen or narrow the hollow, whereby a bracket attachment from the outer edge line to the inner sides of target teeth for an orthodontic treatment is accomplished in an easy, simple and simultaneous format.

2. The orthodontic bracket positioning system of claim 1 wherein the actuator comprises a support having a mid portion, a first end and a second end, wherein the first and second ends are sequentially engaged to the respective rear ends of the first and second connectors, wherein a rotation of the support enables the rear ends of the first and second connectors to become either closer to or farther from each other.

3. The orthodontic bracket positioning system of claim 2 wherein the support is a cylindrical rod, wherein the support is threaded on and along the first and second ends thereof, wherein helical threadings of the threaded first and second ends are opposed to each other in direction.

4. The orthodontic bracket positioning system of claim 2 wherein the actuator further comprises a handle fixed between the first and second ends to the support to easily manipulate the rotation of the support.

5. The orthodontic bracket positioning system of claim 1 wherein said each side portion of the plate includes one or more openings therethrough to facilitate the bracket positioning along the outer ridge line of the plate.

6. The orthodontic bracket positioning system of claim 1 wherein the plate is formed of a metallic material.

7. The orthodontic bracket positioning system of claim 1 wherein the bridge is substantially equivalent to said each side portion of the plate in thickness.

8. The orthodontic bracket positioning system of claim 1 wherein the bridge is substantially shaped in an arc.

9. An orthodontic bracket positioning system comprising:
a) a plate having a bridge, wherein the plate is defined by a first side portion and a second side portion to form a hollow therebetween wherein the first and second side portions are connected to each other by the bridge, wherein an outer edge line of the plate contains therein the bridge, the first and second side portions;
b) first and second connectors each having a front end and a rear end, wherein the first and second connectors are rotatably engaged to each other between the front and rear ends thereof, wherein the first connector front end is rotatably connected to the first side portion and the second connector front end is rotatably connected to the second side portion of the plate;
c) an actuator engaged to said each rear end of the first and second connectors to control a relative rotation of the first and second connectors so as to subsequently either widen or narrow the hollow, whereby a bracket attachment from the outer edge line to inner sides of target teeth for an orthodontic treatment is accomplished in an easy, simple and simultaneous format; and
d) a frame having a control arm to facilitate the bracket attachment, wherein the control arm is detachably engaged to the actuator for accuracy and stabilization of the bracket attachment.

10. The orthodontic bracket positioning system of claim 9 wherein the actuator comprises a support having a mid portion, a first end and a second end, wherein the first and second ends are sequentially engaged to the respective rear ends of the first and second connectors, wherein a rotation of the support enables the rear ends of the first and second connectors to become either closer to or farther from each other.

11. The orthodontic bracket positioning system of claim 10 wherein the support is a cylindrical rod, wherein the support is threaded on and along the first and second ends thereof, wherein helical threadings of the threaded first and second ends are opposed to each other in direction.

12. The orthodontic bracket positioning system of claim 9 wherein the actuator further comprises a handle fixed between the first and second ends to the support to easily manipulate the rotation of the support.

13. The orthodontic bracket positioning system of claim 9 wherein said each side portion of the plate includes one or more openings therethrough to facilitate the bracket positioning along the outer ridge line of the plate.

14. The orthodontic bracket positioning system of claim 9 wherein the plate is formed of a metallic material.

15. The orthodontic bracket positioning system of claim 9 wherein the bridge is substantially equivalent to said each side portion of the plate in thickness.

16. The orthodontic bracket positioning system of claim 9 wherein the bridge is substantially shaped in an arc.

* * * * *